United States Patent
Kuzma

[19]

[11] Patent Number: 6,125,302
[45] Date of Patent: Sep. 26, 2000

[54] PRECURVED MODIOLAR-HUGGING COCHLEAR ELECTRODE

[75] Inventor: Janusz A. Kuzma, Englewood, Colo.

[73] Assignee: Advanced Bionics Corporation, Sylmar, Calif.

[21] Appl. No.: 09/140,035

[22] Filed: Aug. 26, 1998

Related U.S. Application Data

[60] Provisional application No. 60/056,055, Sep. 2, 1997, and provisional application No. 60/061,945, Oct. 14, 1997.

[51] Int. Cl.⁷ .................................................. A61N 1/05
[52] U.S. Cl. ............................................................ 607/137
[58] Field of Search ..................................... 607/136, 137

[56] References Cited

U.S. PATENT DOCUMENTS

| | | | |
|---|---|---|---|
| 4,819,647 | 4/1989 | Byers et al. | 128/642 |
| 4,832,051 | 5/1989 | Jarvik et al. | 128/784 |
| 4,898,183 | 2/1990 | Kuzma | 128/784 |
| 5,000,194 | 3/1991 | van den Honert et al. | 128/784 |
| 5,037,497 | 8/1991 | Stypulkowski | 156/245 |
| 5,443,493 | 8/1995 | Byers et al. | 607/137 |
| 5,545,219 | 8/1996 | Kuzma | 623/10 |
| 5,578,084 | 11/1996 | Kuzma et al. | 623/10 |
| 5,603,726 | 2/1997 | Schulman et al. | 607/57 |
| 5,630,839 | 5/1997 | Corbett, III et al. | 607/137 |
| 5,645,585 | 7/1997 | Kuzma | 623/10 |
| 5,649,970 | 7/1997 | Loeb et al. | 607/57 |
| 5,653,742 | 8/1997 | Parker et al. | 607/137 |
| 5,667,514 | 9/1997 | Heller | 606/108 |

*Primary Examiner*—Scott M. Getzow
*Attorney, Agent, or Firm*—Bryant R. Gold

[57] ABSTRACT

An electrode array has an elongate flexible carrier that, when viewed in cross-section, is much more flexible in a first direction than in a second direction orthogonal thereto. The elongate flexible carrier is formed with a bias force that causes the array to flex in the first direction so as to assume the general spiral or circular shape of the scala tympani duct within the cochlea. The less-flexible direction is the direction that makes it difficult for the array to twist as it is inserted within the scala tympani duct. The bias force is sufficiently strong to cause the array to assume its preformed spiral shape even after being straightened during initial insertion into the cochlea. Electrode contacts, embedded into the carrier so as to be exposed along an inner or concave surface of the spiral, thus wrap snugly around the modiolus, thereby positioning the electrode contacts against the modiolar wall in an optimum position for stimulation.

12 Claims, 5 Drawing Sheets

PRECURVED MODIOLAR-HUGGING COCHLEAR ELECTRODE

This application claims the benefit of U.S. Provisional Patent Applications Ser. No. 60/056,055, filed Sep. 2, 1997; and Ser. No. 60/061,945, filed Oct. 14, 1997.

BACKGROUND OF THE INVENTION

The present invention relates to implantable stimulation devices, e.g., cochlear prosthesis used to electrically stimulate the auditory nerve, and more particularly to an electrode array for use with a cochlear stimulator that is designed to hug the modiolus so as to place electrode contacts of the electrode array in close proximity to the ganglion cells and thereby to the auditory nerve fibers.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlear (the hair cells are located in the vicinity of the radially outer wall of the cochlea) by presenting electrical stimulation to the auditory nerve fibers directly, leading to the perception of sound in the brain and an at least partial restoration of hearing function. The common denominator in most of these cochlear prosthesis systems has been the implantation, into the cochlea of electrodes which are responsive to suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode shown in the '647 patent represents a significant advance in the art, there exists lack of sufficient shape memory associated with the electrode to allow it to return to its original curvature (once having been straightened for initial insertion) with sufficient hugging force to allow it to wrap snugly against the modiolus of the cochlea.

It is also known in the art, as shown in applicant's prior patents, U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference.

Unfortunately, while the electrode array taught in the above-referenced '219 and '585 patents has the right idea, i.e., to force the electrode carrier into a close hugging engagement with the modiolus, it does so only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

Thus, while it has long been known that an enhanced performance of a cochlear implant can be achieved by proper placement of the electrode contacts close to the modiolar wall of the cochlea, two main problems have faced designers in attempting to achieve this goal. First, it is extremely difficult to assemble electrode contacts on the medial side of the an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes are generally positioned too far way from the modiolar wall.

It is thus evident that improvements are still needed in cochlear electrodes, particularly to facilitate assembling an electrode so that the electrode contacts are on the medial side of the electrode array, and to better assure that the electrode assumes a close hugging relationship with the modiolus once implantation of the electrode has occurred.

SUMMARY OF THE INVENTION

The present invention addresses the above and other needs by providing an electrode array that is fabricated in a straight shape using simple tools and basic techniques. Moreover, the electrode array of the present invention is fabricated to assume a pre-programmed spiral shape (i.e., a precurved shape) with sufficient memory so that even after initial straightening (to facilitate implantation) it recovers its precurved shape with sufficient force so that it tightly wraps snugly around the modiolus.

In accordance with one aspect of the invention, an electrode array adapted for implantation within a cochlea is provided that comprises: (a) an elongate flexible silastic carrier that, when viewed in cross-section, is much more flexible in a first direction than in a second direction orthogonal to the first direction, and wherein the silastic carrier has a memory or bias formed therein that causes the carrier to assume a spiral shape which curves in the first direction so that a first surface of the carrier resides along an inner concave surface of the spiral shape; (b) a plurality of electrode contacts embedded within the flexible carrier, a portion of each contact being exposed at the first surface of the carrier; and (c) conductor means (e.g., wires) embedded within the flexible carrier for making electrical contact with each of the plurality of electrode contacts. Thus, when implanted in the cochlea, the bias formed within the electrode array causes the electrode array to assume its spiral shape, thereby positioning its first surface, and hence the electrode contacts, snugly against a modiolar wall of the cochlea.

In accordance with another aspect of the invention, the elongate flexible silastic carrier of the electrode array has a passageway or lumen passing longitudinally therethrough. Such passageway or lumen advantageously allows a stylet, or other equivalent positioning device, to be placed within the passageway so as to help guide insertion of the silastic carrier into the cochlea during implantation.

It is thus a feature of the present invention to provide an electrode array for use with a cochlear stimulator that is easily fabricated in a straight shape using simple tools and basic manufacturing techniques.

It is another feature to provide a precurved electrode array that has sufficient memory so as to recover its precurved shape after initial straightening with sufficient force to allow it to wrap snugly around the modiolus, thereby positioning the electrode contacts in the optimal position within the cochlear.

It is a further feature of the invention to provide an electrode array that hugs the modiolus, placing contact faces of the electrodes used within such array in close proximity to ganglion cells of the auditory nerve.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
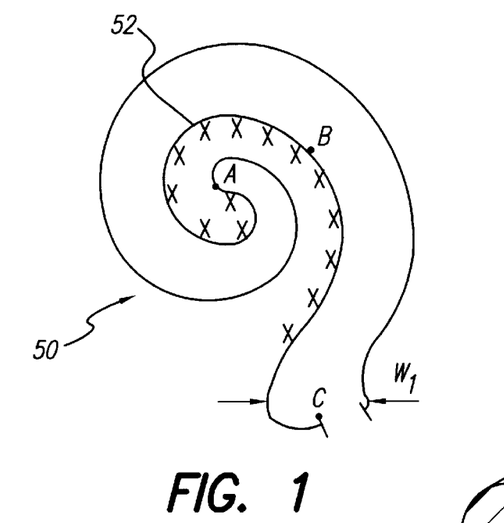
FIG. 1 shows the schematic structure of the cochlea.

Referring to FIG. 1, there is shown the schematic structure of human cochlea 50. The section of the cochlea from point A to point B, i.e., section AB, has a spiral shape. In contrast, the section from point B to point C, i.e., section BC, is almost straight. The area of stimulation, i.e., the location of the ganglion cells, is marked with X's. It is an object of the present invention to provide an electrode array wherein the stimulating contacts, i.e., the electrode contacts, are positioned in close proximity to the spiral ganglion cells XXX.

Figure 2A:
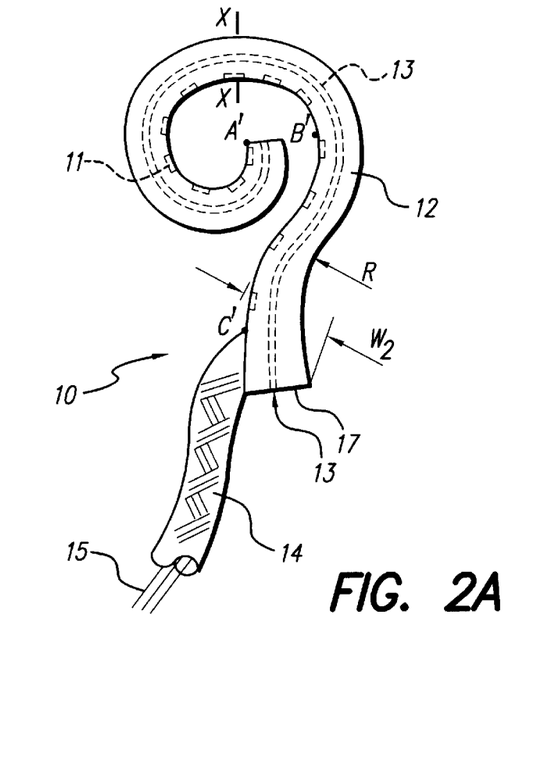
FIG. 2A illustrates a precurved electrode array made in accordance with the present invention.
Figure 2B:
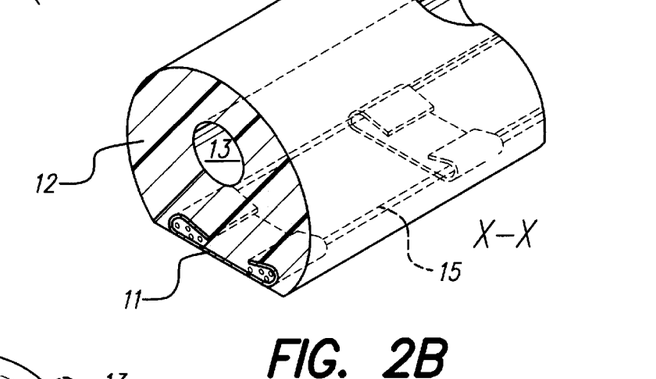
FIG. 2B shows a cross sectional view of the array of FIG. 2A taken along the line X—X in FIG. 2A.

To this end, an electrode array 10 is provided as shown in FIGS. 2A and 2B. As seen in FIG. 2A, the array 10 comprises a precurved electrode array having the same general curvature as that of the cochlea 50. The array 10 includes an elongate silastic flexible carrier 12 having an array of platinum electrode contacts 11 connected to corresponding insulated wires 15. The elongate silastic flexible carrier 12 has a hole or lumen 13 passing therethrough. The wires 15 exit the silastic carrier 12 near a proximal end thereof and form a cable 14 that connects with a cochlear stimulator (not shown). The cochlear stimulator is thus able to make electrical connection with each of the electrode contacts 11 through respective ones of the wires 15.

The electrode contacts 11 of the array 10 are positioned along the medial electrode wall following the line between points A', B' and C'. This line, as seen in FIG. 2A, is along an inner side of the array 10, along a portion of the curve or spiral that is generally concave. This side of the array carrying the electrodes 11 is designed to be positioned against the modiolar wall 52 of the cochlea (FIG. 1), which is the inner surface (or the inside surface of the cochlea having the tightest spiral).

FIG. 2B shows a cross sectional view of the array 10 of FIG. 2A taken along the line X—X in FIG. 2A. Advantageously, the carrier 12 is designed so as to exhibit very low stiffness in the direction Y—Y (the plane of the spiral), whereas it exhibits much greater stiffness in the lateral direction X—X. As explained below, the carrier 12 is constructed so as to have a built-in bias or memory force which forces the carrier to naturally assume spiral or curved shape shown in FIG. 2A.

As seen best in FIG. 2B, the carrier 12 has a passage way (also referred to herein as a "hole" or "lumen") 13 along the entire length of the electrode.

The spiral shape of the electrode 10 between points A' and B' is equal to, or a little smaller than (i.e., has a radius of curvature smaller than) the cochlear curve between cochlear points A and B (see FIG. 1). Section B'C' of the silastic carrier 12, in contrast, preferably has a reversed curve having a reversed radius R such that the distance W2 (FIG. 2A) is the same as, or slightly larger than, the distance W1 across the entrance of the cochlea (see FIG. 1). Advantageously, the carrier 12 has sufficient memory stored in the silastic material from which it is made to force the silastic carrier to return to the desired curvature, e.g., as shown in FIG. 2A, after being straightened during the insertion process.

Figures 3A, 3B:
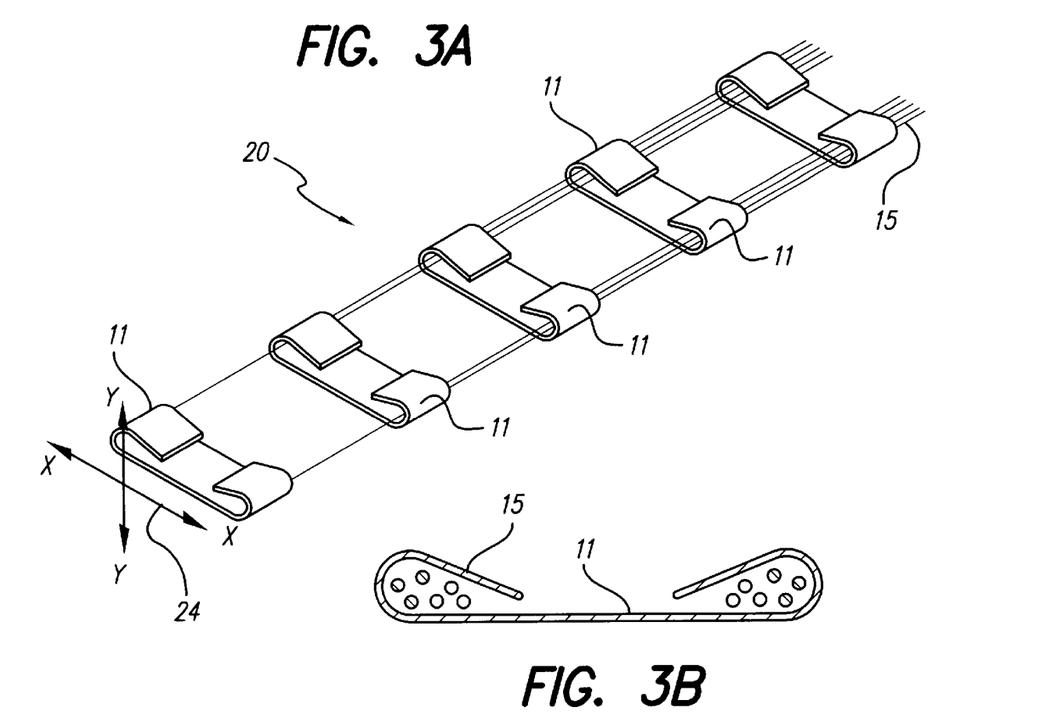
FIG. 3A depicts an assembly of electrode contacts and wires used as part of the method of making an electrode array in accordance with the present invention.
FIG. 3B shows a cross sectional view of FIG. 3A, and illustrates how the wires on each side of an electrode are held in place by the folded ends of each contact.

An important feature of the present invention is that the electrode array may be fabricated in a straight shape using simple tools and basic techniques. FIG. 3A, for example, depicts an assembly 20 of electrode contacts 11 and wires 15 used as part of the method of making an electrode array 10 in accordance with the present invention. The electrode contacts 11 are preferably made from platinum (Pt) strips connected with 25 micron diameter platinum-iridium (Pt—Ir) insulated wires 25 placed on each side of the strip. FIG. 3B shows a cross sectional view of the assembly 20 of FIG. 3A. As seen in FIG. 3B, the wires 15 on each side of an electrode contacts 11 may be held in place by the folded ends of each contact. The wires 25 are placed in two identical bundles on each side, making the array very flexible in direction Y—Y, and many times stiffer in direction X—X. This bundled-pair configuration also provides redundancy in the electrical paths to each electrode contact, thereby enhancing the reliability of the electrode array.

The dimensions shown in FIGS. 3A and 3B (as well as the other figures) are in millimeters. These dimensions are intended to show representative dimensions, and are not intended to be limiting.

The two wires 25 (one on each side) that make electrical contact with their respective electrode contact 11 may be physically connected to the individual contact strip using any suitable technique, e.g., spot welding, brazing, crimping, or the like.

Figure 4:
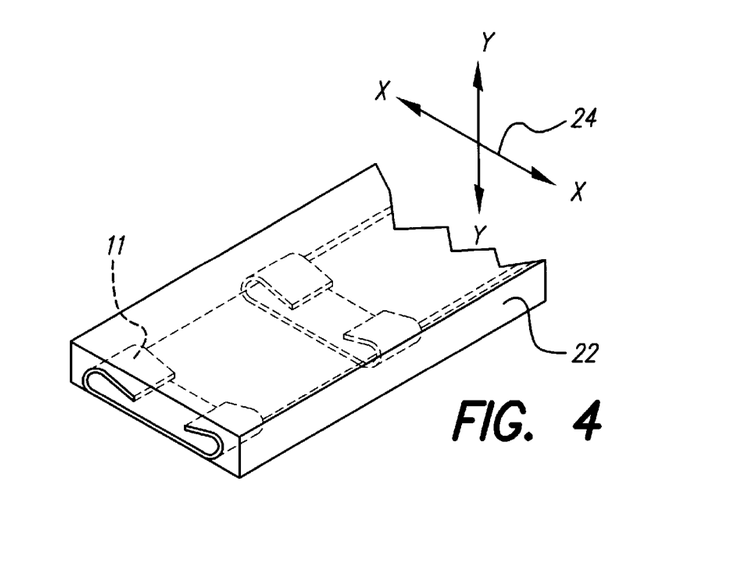
FIG. 4 shows the assembly of FIG. 3A after being pre-molded in silicone polymer.

Once the electrode/wire assembly 20 has been assembled, as shown in FIGS. 3A and 3B, the assembly may be pre-molded in silicone polymer, or other suitable material, to form a stable strip 22, as shown in FIG. 4. The surface of the individual electrode contacts 11 preferably remains exposed on the underside of the strip 22 (as positioned in FIG. 4). Again, this strip 22 is very flexible in the direction Y—Y, but is many times stiffer in the direction X—X. Note that the directions "X" and "Y" are defined in FIGS. 3A and 4 by the X-Y coordinate system 24 shown in these figures.

Figure 5:
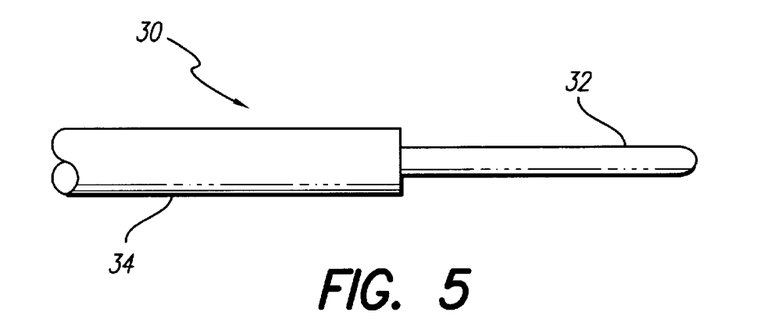
FIG. 5 shows a side view of a mandrel that is used as a tool in forming the electrode array of the present invention.

In order to provide the memory feature of the electrode array, i.e., in order to provide a built-in biasing force that maintains the electrode in its desired spiral shape, a mandrel 30 is constructed as shown in FIG. 5. The mandrel 30 includes a tip portion 32 and a handle portion 34. The tip portion is typically about 20 mm in length and has a diameter of about 0.50 mm. The tip portion 32 is coated with a TEFLON sleeve having an overall diameter of 0.45 mm. Thus, the TEFLON sleeve must typically be stretched to fit over the 0.50 mm diameter tip portion.

Figure 6:
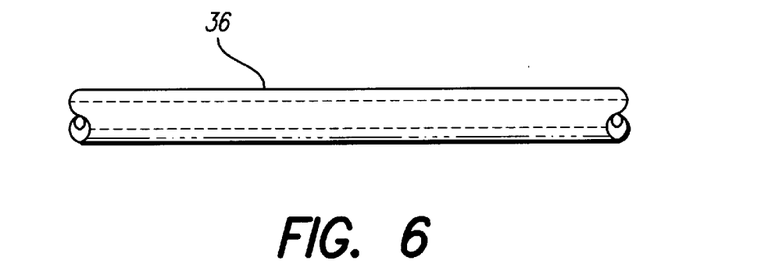
FIG. 6 illustrates a silastic tube.
Figure 7:
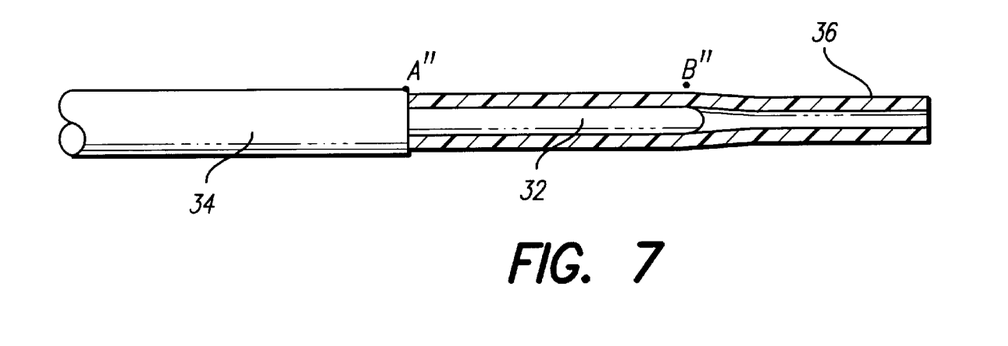
FIG. 7 shows the tube of FIG. 6 after being pushed onto the mandrel of FIG. 5 and compressed a prescribed amount.

Turning next to FIG. 6, a silastic tube 36 is cut to a length of about 50 mm. The silastic tube 36 typically has an outer diameter (OD) of about 0.64 mm, and an inner diameter (ID) of about 0.30 mm. As seen in FIG. 7, the tube 36 is pushed gradually onto the oversized tip 32 of the mandrel 30 and is compressed in length by approximately 30% in distance between points A" and B". As a result, about 30 mm of tubing is stored on the 20 mm (A"-B") section of the mandrel tip. It is this compression which advantageously provides stored energy within the carrier 12 that ultimately gives the array 10 its spiral shape.

Figure 8A:
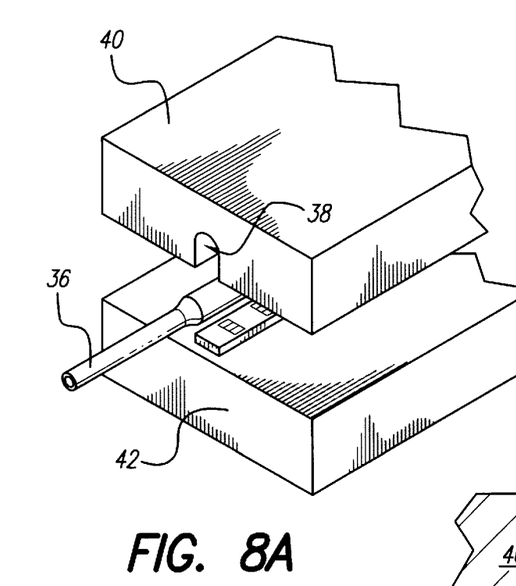
FIG. 8A shows a perspective view of the contact array of FIG. 3A and/or FIG. 4 along with the compressed silastic tube on the mandrel of FIG. 7 as placed within the cavity of a two-part molding die, prior to injecting a silicone polymer into the cavity.
Figure 8B:
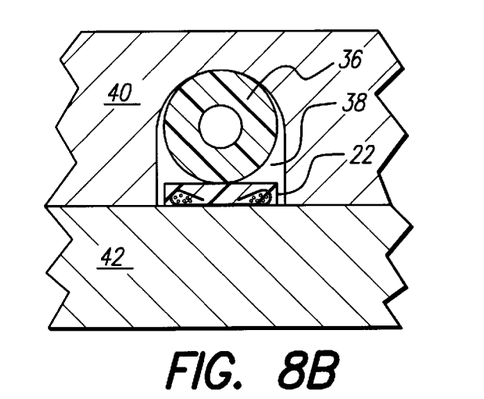
FIG. 8B shows a sectional view of the array and tube as held into place within the molding die.
Figure 9:
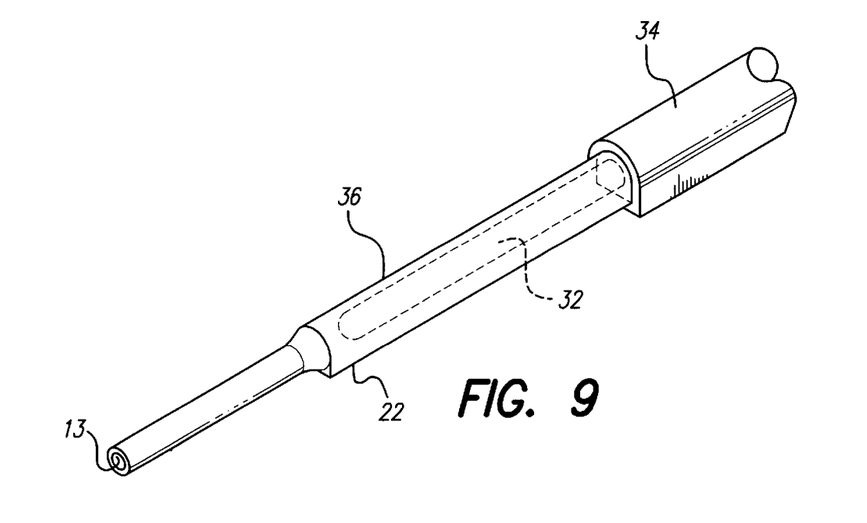
FIG. 9 illustrates the electrode after curing of the silicone polymer.

After compressing the silastic tube 36 onto the tip 32 of the mandrel 30, the compressed tube and the contact/wire assembly 20 (whether premolded into a strip 22 as shown in FIG. 4 or not) are placed in a cavity 38 of a two-part molding die 40, 42, as shown in FIG. 8A and FIG. 8B. The mold cavity 38 is then filled or injected with a liquid two-part silicone polymer, thereby filling the gaps between the tube 36 and the contact/wire assembly 20 (or remolded strip 22), fusing the two parts together. After curing, the electrode array is removed from the die in a straight shape as maintained by the tip 32 of the mandrel, as shown in FIG. 9. The silastic tube 36, with the contact/wire assembly 20, or premolded strip 22, as fused together within the cavity 38 of the molding die 40, 42 by the silicone polymer, thus form the elongate flexible carrier 12 previously described in connection with FIGS. 2A and 2B. The lumen through the tube 36 becomes the opening or passageway 13 that passes through the carrier 12.

Figure 10:
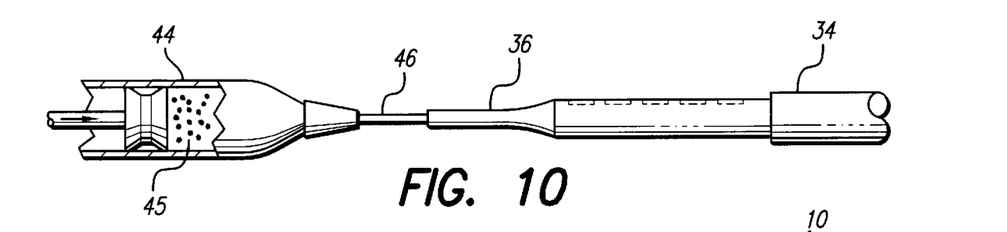
FIG. 10 depicts the manner in which a syringe with needle can be used to pump a suitable releasing agent, such as alcohol, into the open end of the tube, thereby facilitating removal of the mandrel from the tube hole.
Figure 11:
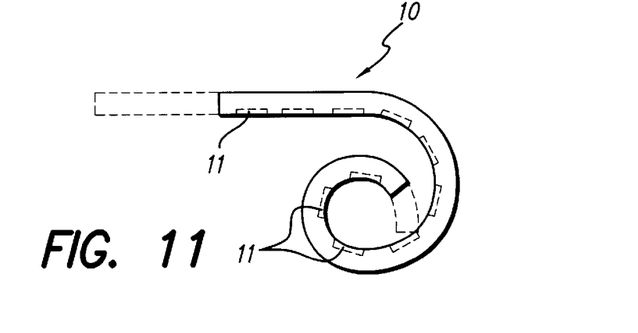
FIG. 11 shows the electrode array after removal of the mandrel, and illustrates how the compressed energy stored in the tube, curves the array to the desired shape.

Next, as shown in FIG. 10, a syringe 44 filled with a suitable releasing agent 45, such as alcohol, is connected to the open end of the tube 36 via a needle 46. The releasing agent is then pumped into the open end of the tube 36, allowing easy removal of the mandrel tip 32 from the tube hole 13. As soon as the mandrel tip 32 is removed, the electrode array 10, as a result of the energy stored in the compressed tube 36, curves to the desired shape, as shown in FIG. 11. The amount of curvature of the electrode array 10 may be controlled by the selection of the hardness of the tubing 36 and the degree of compression placed on the tube 36 as it is pushed onto the mandrel tip 32.

The reverse curvature of the electrode array for the B'-C' portion (see FIG. 2A) may be formed using one of at least two methods. First, the section of the tube on the mandrel corresponding to the portion B'-C' may be stretched, while still maintaining a compression for the section corresponding to the portion A'-B'. When released from the mandrel tip, the section B'-C' will thus be curved in the opposite direction to that of section A'-B'. Second, as an alternate method, the released, molded electrode may be placed on the mandrel, and the mandrel may be bent with the electrode to the desired shape. Then, a layer of silicone polymer can be added on the lateral side (shown by "R" in FIG. 2A). Because, this B'-C' section of the tube 36 has no compression, it can be modified using this alternative approach.

Figure 12:
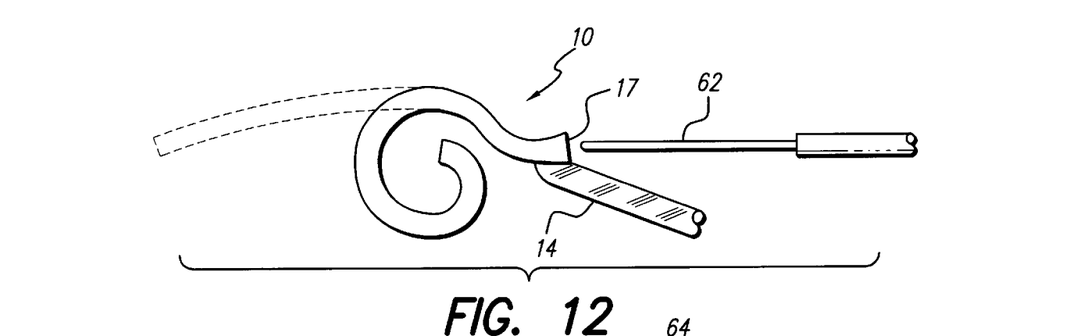
FIG. 12 illustrates the use of a stylet, placed inside of the hole or lumen formed within the array, to straighten the array during an initial phase of inserting the array within the cochlea.

Once formed, the electrode array 10 of the present invention may be easily inserted into the cochlea. To perform such insertion, it is first necessary to straighten the electrode. This may be done by placing a straightening stylet inside the hole or passageway 13 of the electrode array, as shown in FIG. 12. Such a stylet is very useful to help guide the electrode into the cochlea.

Figure 13A:
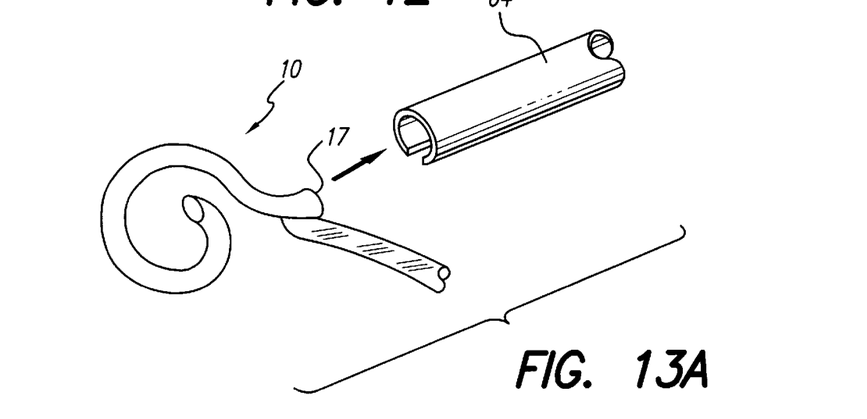
FIG. 13A and 13B illustrate the use of an insertion tube used in conjunction with, or as a alternative to, the use of a stylet as shown in FIG. 12 to assist in straightening and inserting the array into the cochlea.
Figure 13B:
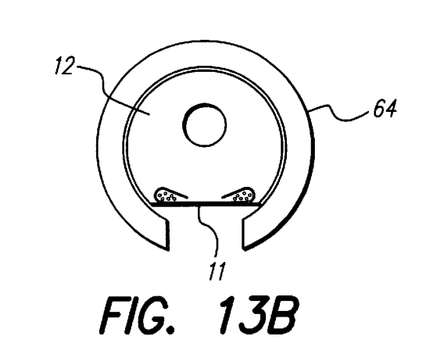

Alternatively, or in combination with using a stylet 62, the electrode array 10 may be loaded into an insertion tube 64 as shown in FIGS. 13A and 13B.

Regardless of the which technique is used, i.e., the stylet 62 (FIG. 12) or/and the insertion tube 64 (FIGS. 13A, 13B), the electrode array in its straightened condition, is inserted within the first section of the cochlea up to point B (see FIG. 1), where the cochlea channel is starting to curve. Then, the electrode array is pushed off of the stylet 62, and/or extracted out of the insertion tube 64, until the tip of the electrode array reaches point A within the cochlea. Such pushing or extraction is facilitated by the shoulder 17 formed at the proximal end of the carrier 12, which shoulder provides a convenient surface against which a pushing or extraction force may be applied.

Once the tip of the electrode array has reached point A, the stylet 62 and/or insertion tube 64, used to hold the electrode array 10 in place, may be completely withdrawn, and the implantation of the electrode array is complete.

As described above, it is thus seen that the present invention provides an electrode array for use with a cochlear stimulator that is easy to manufacture, easy to insert or implant within the cochlea, and which resists twisting. It is further seen that the invention provides such an electrode array wherein the electrode contacts hug the modiolus, placing contact faces of the electrodes used within the array in close proximity to ganglion cells of the auditory nerve.

While the invention herein disclosed has been described by means of specific embodiments and applications thereof, numerous modifications and variations could be made thereto by those skilled in the art without departing from the scope of the invention set forth in the claims.

What is claimed is:

1. An electrode array adapted for insertion into a cochlea for use with a stimulation device comprising:

a flexible carrier formed to assume a precurved shape;

a plurality of spaced-apart electrode contacts embedded within the flexible carrier, a portion of each contact being exposed at a first surface of the carrier;

the first surface of the carrier comprising that surface which assumes an inner surface of the curved shape; and a lumen passing longitudinally through the flexible carrier through which a stylet may be placed to help guide insertion of the flexible carrier into the cochlea during implantation.

2. The electrode array of claim 1 wherein the precurved shape of the flexible carrier corresponds to the curvature of the cochlea and wherein the flexible carrier recovers said precurved shape after straightening with sufficient force so that when the electrode array is inserted into the cochlea the electrode contacts are positioned snugly against an inside surface of the cochlea.

3. An electrode array adapted for implantation within a human cochlea, comprising:

an elongate flexible carrier that, when viewed in cross-section, is much more flexible in a first direction than in a second direction orthogonal to the first direction;

a plurality of electrode contacts embedded within the carrier, each being electrically connected to a respective wire that is also embedded within the carrier;

a passageway passing through the elongate flexible carrier into which a stylet may be removably inserted to straighten the elongate flexible carrier during implantation; and wherein said elongate flexible carrier has compression energy stored therein that forces the carrier to assume a precurved shape in the first direction.

4. The electrode array of claim 3 wherein the plurality of electrode contacts are positioned along a first surface of the carrier that is on the inside of the curve, whereby when said electrode array is inserted into the cochlea, and the curvature of the electrode array is oriented to match the curvature of the cochlea, the plurality of electrode contacts hug an inner surface of the cochlea.

5. A precurved cochlear electrode array, comprising:

an elongate flexible carrier adapted for insertion into a human cochlea, wherein the flexible carrier is formed in a precurved shape, and wherein sufficient bias force is present within the elongate flexible carrier to return the elongate flexible carrier to the precurved shape after an initial straightening;

a plurality of electrode contacts and wires embedded within the carrier, each electrode contact being electrically connected to at least one wire, wherein electrical contact is made with each electrode contact through at least one of the wires; and a passageway passing longitudinally through the elongate flexible carrier, the passageway providing a channel into which a stylet may be placed to straighten the elongate precurved flexible carrier during insertion of the elongate flexible carrier into the cochlea.

6. The precurved cochlear electrode array of claim 5 wherein each electrode contact is exposed on a medial wall of the precurved elongate flexible carrier, wherein the medial wall of the precurved flexible carrier comprises that surface of the elongate flexible carrier on the inside of the curve defined by the precurved shape of the flexible carrier, and is that surface which is adapted to be positioned against a modiolar wall of the cochlea when the precurved cochlear electrode array is inserted into the cochlea.

7. The precurved cochlear electrode array of claim 5 wherein the precurved elongate flexible carrier, with wires and electrodes embedded therein, is adapted to exhibit low stiffness in the direction Y—Y, and greater stiffness in direction X—X, where the direction Y—Y and the direction X—X are defined by a cross-sectional view of the elongate flexible carrier in which the electrode contacts are located on the bottom of said cross-sectional view, and the direction Y—Y is the vertical direction of said cross-sectional view, and the direction X—X is the horizontal direction of said cross-sectional view.

8. The precurved cochlear electrode array of claim 7 wherein the wires embedded within the elongate flexible carrier are placed in two bundles, one bundle being located on each side of a cross section of the elongate flexible carrier.

9. The precurved cochlear electrode array of claim 7 wherein the wires embedded within the elongate flexible carrier provide redundant electrical paths to each electrode contact.

10. A cochlear electrode system comprising a precurved cochlear electrode array; and means for straightening the precurved electrode array to facilitate insertion of the precurved electrode array into a human cochlea;

wherein the precurved electrode array comprises:

an elongate flexible carrier formed in a precurved shape, wherein sufficient bias force is present within the elongate flexible carrier to return the elongate flexible carrier to the precurved shape after being straightened, and a plurality of electrode contacts and wires embedded within the elongate flexible carrier, each electrode contact being electrically connected to at least one wire, wherein electrical contact is made with each electrode contact through at least one of the wires.

11. The cochlear electrode system of claim 10 wherein the means for straightening the precurved electrode array comprises:

a stylet; and a passageway passing longitudinally through the elongate flexible carrier, the passageway providing a channel into which the stylet is placed to straighten the precurved shape of the elongate flexible carrier during insertion of the precurved cochlear electrode array into the cochlea.

12. The cochlear electrode system of claim 10 wherein the means for straightening the precurved electrode array comprises an insertion tube.

\* \* \* \* \*